US007713956B2

United States Patent
Carminati et al.

(10) Patent No.: US 7,713,956 B2
(45) Date of Patent: May 11, 2010

(54) DEALKYLATED DERIVATIVES OF PYRROLO[2,1-B]BENZOTHIAZEPINES WITH ATYPICAL ANTIPSYCHOTIC ACTIVITY

(75) Inventors: Paolo Carminati, Milan (IT); Maria Assunta Di Cesare, Rome (IT); Orlando Ghirardi, Rome (IT); Patrizia Minetti, Rome (IT); Maria Ornella Tinti, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 805 days.

(21) Appl. No.: 11/579,806

(22) PCT Filed: Apr. 28, 2005

(86) PCT No.: PCT/IT2005/000246

§ 371 (c)(1),
(2), (4) Date: Nov. 7, 2006

(87) PCT Pub. No.: WO2005/108403

PCT Pub. Date: Nov. 17, 2005

(65) Prior Publication Data
US 2007/0270402 A1 Nov. 22, 2007

(30) Foreign Application Priority Data
May 7, 2004 (IT) .................. RM2004A0222

(51) Int. Cl.
*A61P 25/18* (2006.01)
*A61K 31/407* (2006.01)
*C07D 513/04* (2006.01)

(52) U.S. Cl. .................. 514/211.12; 540/551
(58) Field of Classification Search ............ 514/211.12; 540/551
See application file for complete search history.

(56) References Cited

FOREIGN PATENT DOCUMENTS
WO 00/06579 A 2/2000

OTHER PUBLICATIONS

Campiani et al; "Pyrrolo '1,3!benzothiazepine-Based Serotonin and Dopamine Receptor Antagonists. Molecular Modeling, Further Structure-Activity Relationship Studies, and Identification of Novel Atypical Antipsychotic Agents", Journal of Medicinal Chemistry, 47(!), 143-157, XP002354023, 2004.
Campiani et al., "Pyrrolo'1!benzothiazepine-Based Atypical Antipsychotic Agents. Synthesis, Structure-Activity Relationship, Molecular Modeling, and Biological Stufies", Journal of Medicinal Chemistry, 45(2), 344-359, XP002354024, 2002.
Campiani et al; "New antipsychotic agents with serotonin and dopamine antagonist properties based on a pyrrolo'2,1-b!'1, 2!benzothiazepine structure", Journal of Medicinal Chemistry, 41(20), 3763-3772, XP002354025, 1998.
International Search Report of PCT/IT2005/000246, Nov. 25, 2005.

*Primary Examiner*—Brenda L Coleman
(74) *Attorney, Agent, or Firm*—Lucas & Mercanti, LLP

(57) ABSTRACT

Derivatives of pyrrolo[2,1-b]benzothiazepines with formula (I) where A is CH—$CH_2$C=CH; R is hydrogen, halogen, $C_1$-$C_4$ alkoxy, $C_1$-$C_4$ alkylthio, $C_1$-$C_4$ alkyl, $C_5$-$C_6$ cycloalkyl; $R_1$ is 1-peperazinyl, 1-homopiperazinyl and 1-piperidinyl; $R_2$ is hydrogen, $C_1$-$C_4$ alkoxy, $C_1$-$C_4$ alkylthio, $C_1$-$C_4$ alkyl, CHO, CH=NOH,$CH_2$OH. The formula (I) compounds are endowed with characteristic atypical antipsychotic activity, and are therefore useful as medicaments, in particular for the treatment and prevention of schizophrenia, paranoid states, manic-depressive states, disorders of the affective sphere, social regression, personality regression, and hallucinations. Said compounds also present advantageous pharmacokinetic properties.

11 Claims, 4 Drawing Sheets

US 7,713,956 B2

DEALKYLATED DERIVATIVES OF PYRROLO[2,1-B]BENZOTHIAZEPINES WITH ATYPICAL ANTIPSYCHOTIC ACTIVITY

This application is the US national phase of international application PCT/IT2005/000246, filed 28 Apr. 2005, which designated the U.S. and claims priority of IT RM2004A000222, filed 7 May 2004, the entire contents of each of which are hereby incorporated by reference.

FIELD OF THE INVENTION

The present invention relates to derivatives of pyrrolo[2,1-b]benzothiazepines with atypical antipsychotic activity, characterised by a good pharmacokinetic profile. The present invention also relates to procedures for the preparation of said compounds, their use as medicaments, in particular as atypical anti-psychotics and to pharmaceutical compositions containing them.

BACKGROUND TO THE INVENTION

The atypical antipsychotics constitute an important class of drugs for the treatment and prevention of psychotic disorders.

Such drugs were proposed as a means for overcoming the problems arising with the use of antipsychotics of the previous generation, namely, the typical antipsychotics, associated with major and severe side effects.

An example of an atypical antipsychotic agent with a favourable therapeutic application is to be found in the class of polycondensed heterocycles with a pyrrolo[2,1-b]benzothiazepine structure described in the international patent applications WO 00/06579 and WO 02/10175, both filed in the name of the present applicant. The first of these applications describes compounds in which, in the thiazepine ring, the bond between carbons 9 and 10 is saturated; conversely, in the second application said bond is unsaturated, and this latter class of compounds is also generically called "enamines". Both classes of compounds have in common, at position 9, a group that can be selected from $C_1$-$C_4$ dialkylamine, 4-alkyl-1-piperazinyl, 4-hydroxyalkyl-1-piperazinyl, 4-alkyl-1-piperidinyl, and 4-alkyl-1-homopiperazinyl. Particularly preferred are compounds bearing, at position 9, one of the groups 4-alkyl-1-piperazinyl, 4-hydroxyalkyl-1-piperazinyl, 4-alkyl-1-piperidinyl, 4-alkyl-1-homopiperazinyl, all commonly characterised by an alkyl group at position 4 of the heterocyclic ring.

In particular, the compound (S)(+) 7-chloro-9-(4-methylpiperazin-1-yl)-9,10-dihydropyrrolo[2,1-b][1,3]benzothiazepine, described in patent application WO 00/06579 and hereinafter referred to for short as ST1460, has demonstrated atypical antipsychotic properties comparable with those of the clinical reference compounds (clozapine and olanzapine) and is associated with lower risks of occurrence of extrapyramidal and/or neuroendocrine effects, characteristic of the typical antipsychotics.

The compound 9-(4-methylpiperazin-1-yl)-pyrrolo[2,1-b]-[1,3]benzothiazepine, described in patent application WO 02/10175 and hereinafter referred to in short as ST1899, also presents favourable pharmacological characteristics and affords the advantage, compared to the preceding compound, of greater activity and greater simplicity of synthesis.

Though endowed with a satisfactory pharmacological profile, the compounds described in the above-mentioned patent applications present kinetics calling for some improvement, in that they are characterised by rapid clearance. It is therefore desirable to have compounds with a similar, if not better, pharmacological profile, but most certainly with an improved pharmacokinetic profile.

SUMMARY OF THE INVENTION

The main object of the present invention is to provide compounds bearing, at position 9, a group selected from 1-piperazinyl or 1-homopiperazinyl, or 1-piperidinyl, that is to say, the dealkylated analogues described in the above-mentioned patent applications, which are endowed with favourable pharmacological activity as atypical antipsychotics and are also characterised by an advantageous pharmacokinetic profile.

A further object of the present invention consists in methods for the preparation of said compounds.

A further object of the present invention consists in the use of said compounds as medicaments, particularly for the preparation of pharmaceutical compositions useful for the treatment and prevention of psychotic, psychiatric and neurological disorders, particularly disorders related to increased activity of the mesolimbic dopaminergic pathway and/or to mesocortical dopaminergic hypofunctionality, such as, for example, schizophrenia in its positive and negative symptoms, paranoid states, manic-depressive states, disorders of the affective sphere, social regression, personality regression, and hallucinations. Said compounds are characterised by atypical antipsychotic activity.

A further object of the present invention consists in pharmaceutical compositions containing at least one compound according to the invention in a mixture with pharmaceutically acceptable vehicles and/or excipients.

The invention will now be described in detail, also with the aid of Examples and Figures.

DETAILED DESCRIPTION OF THE INVENTION

The compounds according to the present invention are described by the following formula (I)

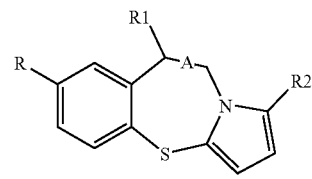

where:
A is CH—$CH_2$ or C=CH;
R is hydrogen, halogen, $C_1$-$C_4$ alkoxy, $C_1$-$C_4$ alkylthio, $C_1$-$C_4$ alkyl, $C_5$-$C_6$ cycloalkyl;
$R_1$ is 1-piperazinyl, 1-homopiperazinyl and 1-piperidinyl;
$R_2$ is hydrogen, $C_1$-$C_4$ alkoxy, $C_1$-$C_4$ alkylthio, $C_1$-$C_4$ alkyl, CHO, CH=NOH, $CH_2OH$;
provided that when R is Cl, A is not C=CH
their single optical isomers, mixtures thereof and their pharmaceutically acceptable salts.

In the case of formula (I) compounds with the saturated thiazepine ring at positions 9 and 10, position 9 is characterised by a chiral centre. The present invention comprises compounds both as racemic mixtures and separately as single isomers (R) and (S).

In formula (I), R represents preferably bromine, chlorine (except when A is C=CH), fluorine or hydrogen, more preferably hydrogen, chlorine or fluorine; $R_1$ is preferably the piperazin-1-yl group and $R_2$ is preferably hydrogen.

Preferred compounds according to the present invention are:

(+)-9-(piperazin-1-yl)-9,10-dihydropyrrolo[2,1-b][1,3]benzothiazepine;

(−)-9-(piperazin-1-yl)-9,10-dihydropyrrolo[2,1-b][1,3]benzothiazepine;

(±)-7-chloro-9-(piperazin-1-yl)-9,10-dihydropyrrolo[2,1-b][1,3]-benzothiazepine (ST2087);

(S)-7-chloro-9-(piperazin-1-yl)-9,10-dihydropyrrolo[2,1-b][1,3]-benzothiazepine (ST2432);

(R)-7-chloro-9-(piperazin-1-yl)-9,10-dihydropyrrolo[2,1b][1,3]-benzothiazepine;

(+)-7-fluoro-9-(piperazin-1-yl)-9,10dihydropyrrolo[2,1b][1,3]-benzothiazepine;

9-(piperazin-1-yl)-pyrrolo[2,1-b][1,3]benzothiazepine (ST2472);

7-fluoro-9-(piperazin-1-yl)-pyrrolo[2,1-b][1,3]benzothiazepine;

1-methyl-9-(piperazin-1-yl)-pyrrolo[2,1-b][1,3]benzothiazepine.

A further subject of the present invention consists in procedures for the preparation of formula (I) compounds. In a first embodiment of the invention, the procedure consists of the following stages:

a) treatment of the corresponding 4-alkyl-(homo)piperazine-1-yl-pyrrolo[2,1-b]benzothiazepine or 4-alkyl-piperidin-1-yl-pyrrolo-[2,1-b]benzothiazepine or 4-alkyl-(homo)piperazine-1-yl-dihydropyrrolo-[2,1-b]benzothiazepine or 4-alkyl-piperidin-1-yl-dihydroppirolo[2,1-b]benzothiazepine, with the desired alkyl-chloroformiate to give the corresponding amide of the nitrogen atom at position 4 of the (homo)piperazine or piperidine ring;

b) subsequent hydrolysis of the carbamate thus obtained, releasing said nitrogen atom;

c) possible salification of the compound obtained in stage b).

Alternatively, the formula (I) compounds can be prepared with the procedure comprising the following stages:

a) treatment of the corresponding ketones at position 9, obtained as described in patent application WO 00/06579 with p-toluenesulphonic acid and piperazine hexahydrate, so as to yield the corresponding enamines;

b) subsequent reduction of the corresponding enamines with hydrides in acetic acid, to yield the corresponding saturated pro-ducts;

c) possible salification of the compound obtained in stage b).

The compounds according to the present invention are easily prepared starting from those described in the above-mentioned patent applications, that is to say, from the corresponding ketones, the synthesis of which is described in patent application WO 00/06579. Once the precursor has been prepared, it is treated according to the procedures of the invention, as illustrated in the following schemes, with examples given for a number of preferred products, but easily generalisable to all formula (I) compounds thanks to the normal general knowledge available to the technician of average experience in the sector.

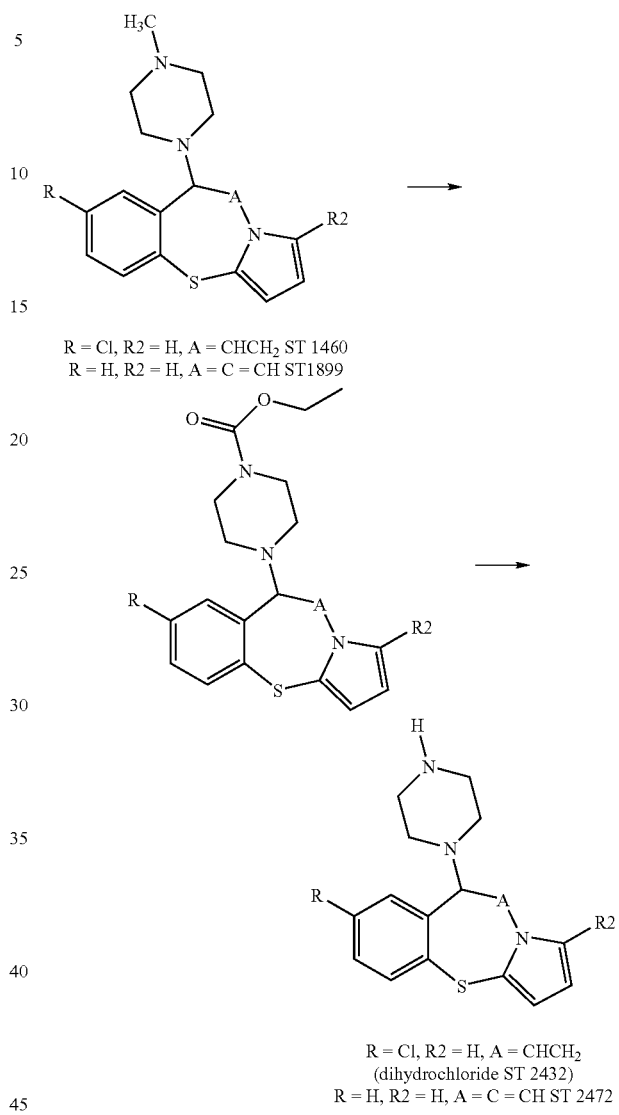

Scheme 1

R = Cl, R2 = H, A = CHCH$_2$ ST 1460
R = H, R2 = H, A = C = CH ST1899

R = Cl, R2 = H, A = CHCH$_2$
(dihydrochloride ST 2432)
R = H, R2 = H, A = C = CH ST 2472

The precursor (e.g., ST1460 or ST1899) is treated with an alkyl-chloroformiate, for example, ethyl-chloroformiate, so as to yield the corresponding carbamate of the nitrogen atom at position 4 of the piperazine ring. The subsequent hydrolysis of the amide thus obtained releases said nitrogen atom. The compound thus obtained can possibly be salified with entirely conventional methods in the art.

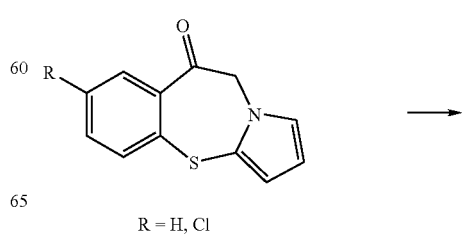

Scheme 2

R = H, Cl

-continued

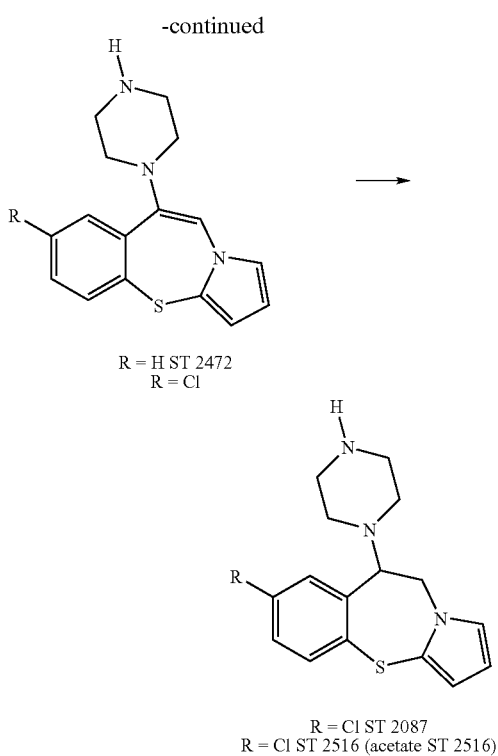

R = H ST 2472
R = Cl

R = Cl ST 2087
R = Cl ST 2516 (acetate ST 2516)

The ketone synthesised as described in patent application WO 00/06579 is treated with p-toluenesulphonic acid and piperazine, so as to yield the corresponding enamine. The subsequent reduction with hydrides in acetic acid yields the corresponding hydrogenated products.

The separation of the single enantiomeric forms can be obtained according to the normal methods with which the expert in the sector is familiar, for example, as described in WO 00/06579.

A further subject of the present invention consists in pharmaceutical compositions containing at least one formula (I) compound in a mixture with pharmaceutically acceptable excipients and/or vehicles and possibly additional active ingredients useful in the treatment and prevention of psychoses, to be used in combination therapy.

For a detailed description of the pharmaceutical compositions, explicit reference is made to patent applications WO 00/06579 and WO 02/10175, particularly with regard to combinations with other active ingredients useful for the treatment and prevention of psychoses.

The compounds according to the present invention are endowed with pronounced antipsychotic activity and possess a pharmacological profile characteristic of the atypical antipsychotics, as demonstrated by the pharmacological assays carried out as described in WO 00/06579 and WO 02/10175, and therefore are useful for the preparation of a medicament for the treatment and prevention of acute and chronic psychotic disorders.

Examples of acute and chronic psychotic disorders which can be treated with the compounds according to the present invention are schizophrenia, paranoid states, manic-depressive states, disorders of the affective sphere, social regression, personality regression, hallucinations, appetite disorders (such as anorexia) and related disorders. Further indications may include analgesia/anaesthesia, neuroleptic anaesthesia, anxiety manifestations in the elderly, and extrapyramidal disorders.

In the particular case of the formula (I) compounds in which the bond between the carbon atoms 9 and 10 is single and R is hydrogen, fluorine, or bromine, these are useful for the preparation of a medicament for the treatment of the negative symptoms of schizophrenia involving the emotional and cognitive spheres, particularly when said negative symptoms take the form of dementia.

In the particular case of the formula (I) compounds in which the bond between the carbon atoms 9 and 10 is unsaturated, these are useful for the preparation of a medicament for the treatment of conditions of hyperactivation of the dopaminergic neurotrans-mission, particularly when this affects the mesolimbic pathway, and/or of conditions of mesocortical dopaminergic hypofunctionality. For example, said conditions take the form of schizophrenia in its positive and negative symptoms.

The formula (I) compounds in which the bond between the carbon atoms 9 and 10 is unsaturated are also indicated for the preparation of a medicament useful for the treatment and prevention of paranoid states, manic-depressive states, disorders of the affective sphere, social regression, personality regression, hallucinations or cognitive dysfunctions.

The formula (I) compounds can be administered over a dosage range that may vary as a rule from 1 to 200 mg/day according to the severity of the disease to be treated and its acute or chronic component. Doses beyond the range indicated can be used, however as decided by the primary care physician.

The compounds according to the present invention are characterised by a favourable pharmacokinetic profile.

The following examples further illustrate the invention.

EXAMPLES

Example 1

Figure 1:
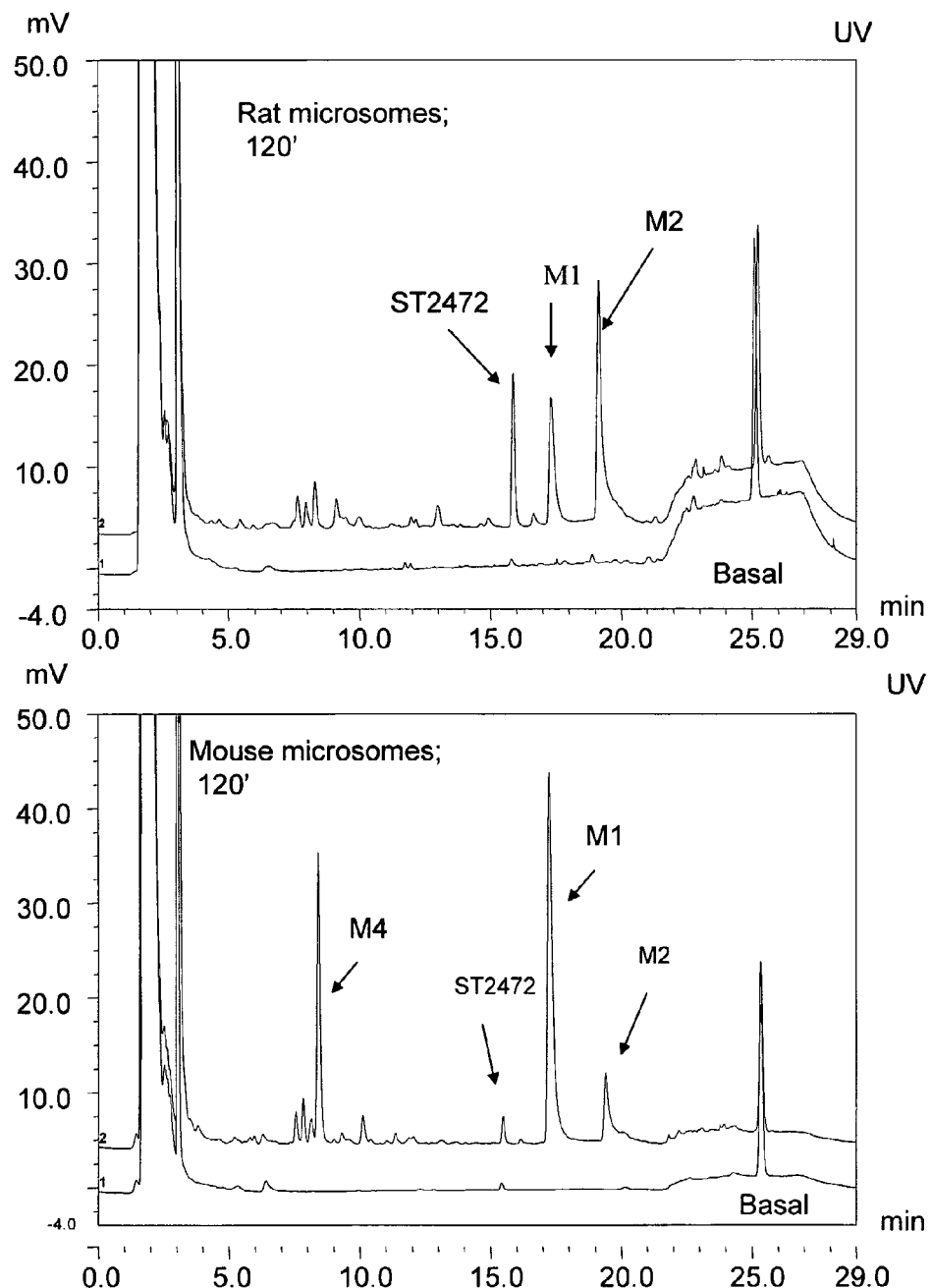
FIG. 1: Metabolic profile obtained for ST1899 in rat and mouse microsomes at 120 minutes in comparison to the basal. Results of the HPLC analysis of the supernatants after incubation with the hepatic microsomes.

Scheme 1 a) Ethyl-4-(7-chloro-9,10-dihydropyrrolo-[2,1-b][1,3]-benzo-thiazepin-9-yl)-1-piperazine-carboxylate ST1460 (mg 340, 1.02 mmol), 1,2-dichloroethane (3 mL), 10 mL of ethyl-chloroformiate and 150 mg of dimethylaminopyridine) were placed in a double-neck 50 mL anhydrous flask equipped with a reflux condenser with calcium chloride cap and thermo-meter. The mixture was maintained under stirring at reflux temperature for three hours.

The reaction mixture was then cooled to room temperature, diluted with methylene chloride (50 mL) and washed with water until neutral pH was obtained (3×50 mL). The methylene solution, anhydrified on sodium sulphate and after evaporation of the solvent, yielded an oil (400 mg) which was purified by chromatography on silica gel (solvent: hexane-ethyl acetate 80:20). 280 mg of the title product were obtained (yield: 70%).

TLC: petroleum ether [40-70]/AcOEt (80:20); Rf: 0.70.

HPLC: LiChrosorb RP-18 (5 μm); water/acetonitrile (40:60); 0.8 mL/min; U.V. λ=MaxAbs; Rt 25.78 min corresponding to the title product.

$^1$H-NMR [CDCl$_3$]: structure within the given range.

$^{13}$C-NMR [CDCl$_3$]: structure within the given range.

b) 1-[(9S)-7-chloro-9,10-dihydropyrrolo[2,1-b][1,3]benzothiazepin-9-yl]piperazinium dichloride (ST2432)

The product obtained in the previous stage (mg 280; 0.715 mmol), n-butanol (5 mL) and potassium hydroxide (mg 400; 7.0 mmol) were placed in a double-neck 50 mL anhydrous flask equipped with a reflux condenser with calcium chloride cap and thermometer. The mixture was stirred at reflux temperature for one hour. Removal of the solvent at reduced pressure yielded an oil which, when purified by chromatography on silica gel (ethyl acetate/methanol gradient: 8:2/6:4), yielded 186 mg of product (yield: 81.3%) which was subsequently chlorhydrated to obtain the title compound.

TLC: methanol/AcOEt/Et$_3$N (1:1+0.5 cc); Rf: 0.15.

HPLC: LiChrosorb RP-18 (5 μm); water/acetonitrile (40:60); 0.8 mL/min; U.V. λ=MaxAbs; Rt: 25.78 min.

$^1$H NMR (CDCl$_3$) δ 7.51 (d, 1H, J=2.4 Hz), 7.30 (d, 1H, J=8.5 Hz), 7.06 (dd, 1H, J=8.5, 2.4 Hz), 6.86 (m, 1H), 6.29 (m, 1H), 6.05 (m, 1H), 4.71 (dd, 1H, J=14.0, 8.6 Hz), 4.45 (dd, 1H, J=14.0, 3.4 Hz), 3.95 (dd, 1H, J=8.6, 3.4 Hz), 2.61-2.25 (m, 8H).

Example 2

Scheme 2 a) 9-Piperazin-1-yl-pyrrolo[2,1-b][1,3]benzothiazepine (ST2472)

190 mg (0.88 mmol) of pyrrolo[2,1-b]benzothiazepin-9(10H)-one, 5.13 g of piperazine hexahydrate (0.026 mol) and 4.53 g (0.024 mol) of p-toluenesulphonic acid were reacted under stirring in a flask. The reaction mixture was heated to a temperature of 180° C. and left to react for 7 hours. The gelatinous mass obtained was dissolved in ethyl acetate and the organic phase was washed three times with water, and then dried on anhydrous sodium sulphate and evaporated. 150 mg of product were obtained which were purified on silica gel, eluting with AcOEt/MeOH 1:1.

43 mg of an oil were obtained

Yield=17.2%

TLC: AcOEt/MeOH/NH$_3$ (1:1:0.3 ml) Rf=0.4

HPLC: LunaCN (5 μm); water/CH$_3$COONH$_4$ (25:75); 1.0 mL/min; U.V. λ=220 nm; Rt: 12.045 min.

$^1$H NMR (CDCl$_3$) δ 7.65 (d, 1H), 7.5 (d, 1H), 7.3 (dd, 2H), 6.75 (m, 1H), 6.6 (s, 1H), 6.2 (m, 1H), 6.1 (m, 1H), 3 (4H,), 2.95 (4H), 2.65 (broad, 1H, NH).

Example 3

Scheme 2 a) 7-chloro-9-(1-piperazinyl)-9,10-dihydropyrrolo[2,1b][1,3]-benzothiazepine acetate (ST2516)

500 mg (1.57 mmol) of 1-[(9S)-7-chloro-9,10-dihydropyrrolo[2,1-b][1,3]benzothiazepin-9-yl]piperazine, (synthesised starting from 7-chloropyrrolo[2,1b][1,3]benzothiazepin-9(10H)-one with the same procedure described in Example 2 for ST2472) were solubilised in a flask equipped with a stirring system in 30 ml of CH$_3$COOH; 400 mg of NaBH$_4$ were added cautiously at 0° C. and left to stir at room temperature for two hours.

The solvent was evaporated under reduced pressure and an oil was obtained which was solubilised in AcOEt, washed twice with NaOH 1 N and finally with H$_2$O; the organic phase was then dried on anhydrous sodium sulphate and the solvent was evaporated.

300 mg of a white solid were obtained (yield: 52%).

Analysis: within the given range for the structure (see ST2432).

Example 4

Scheme 1 a) Ethyl 4-pyrrolo[2,1-b][1,3]benzothiazepin-9-ylpiperazine-1-carboxylate

ST1899 (3 g, 0.01 mol), dissolved in anhydrous methylene (120 mL), and dimethylaminopyridine (DMAP, 1.5 g) were placed in an anhydrous flask; ethyl-chloroformiate (10 mL) was added dropwise to the solution. The reaction mixture was maintained under stirring at room temperature and in a perfectly closed system for five hours. The solvent was then evaporated from the reaction mixture in vacuo with a calcium chloride trap. A white solid was obtained which was purified by chromatography on silica gel (ethyl acetate/hexane—gradient 95:5/80:20). 3 g of the title product were obtained.

Yield=90%.

TLC: (ethyl acetate/hexane 2:8; R$_f$=0.3.

$^1$H NMR (CDCl$_3$) δ 7.65 (d, 1H), 7.5 (d, 1H), 7.3 (dd, 2H), 6.75 (m, 1H), 6.6 (s, 1H), 6.2 (m, 1H), 6.1 (m, 1H), 4.1 (q, 2H), 3.5 (4H,), 2.8 (4H,), 1.2 (t, 1H).

b) 9-piperazin-1-yl-pyrrolo[2,1-b][1,3]benzothiazepine (ST2472)

The product obtained in the previous stage (3 g; 8.9 mmol), n-butanol (22 mL) and potassium hydroxide (4.9 g; 8.9 mmol) were placed in a double-neck 50 mL anhydrous flask equipped with a reflux condenser with calcium chloride cap and thermometer. The mixture was stirred for three hours at reflux temperature. The solvent was removed under reduced pressure, yielding a solid which was solubilised in AcOEt and washed with H$_2$O to neutral pH. The organic phase was then dried on anhydrous sodium sulphate and evaporated. 2 g of product were obtained which, when purified by chromatography on silica gel (ethyl acetate/methanol gradient: 7:3/6:4), yielded 1.5 g of product (yield: 60%).

For analysis: see Example 2 (Scheme 2).

As regards the possible resolution of racemic mixtures, the reader is referred to the description in the above-mentioned patent application WO 00/06579.

Example 5

Pharmacokinetics of the Compound ST1469 and its Corresponding Des Methyl Derivative ST2087

Effect of the Oral Administration of a 60 μmol/kg Dose of Each Product in the Rat Administration of ST1469 in the Rat (Table 1).

Following oral administration of ST1469, the plasma concentrations of the molecule increase until they reach the maximum concentration (Cmax) of approximately 280 pmol/mL, two hours after administration. The elimination of ST1469 is rapid, as can be seen from the half-life which is less than 3 hours.

Metabolism would appear to be the main process of elimination of the product ST1469, as shown by the immediate appearance of its demethylated metabolite (ST2087) which right from the first sample (0.5 h) presents higher plasma concentrations than the product ST1469 as such.

ST2087 reaches its Cmax more slowly (Tmax~3 h) and is also eliminated more slowly than ST1469, (t½~5 h).

Administration of ST2087 in the Rat (Table 1)

After administration of the product ST2087, the absorption rate is comparable to that observed for ST1469, and, in fact, the C max is reached within 2 hours of administration.

The elimination rate of ST2087 remains of the same order of magnitude as that observed for the same molecule, after administration of ST1469.

From this study it emerges that the metabolite administered as such produces, at the systemic level, much higher concentrations than those measured after its formation as a result of administration of ST1469, as demonstrated by the pharmaco-kinetic parameters reported in Table 1.

TABLE 1

Pharmacokinetic parameters of the product ST1469 and the corresponding desmethyl derivative ST2087, after oral administration of a 60 μmol/kg dose of each product in the rat.

| Treatment | Analyte | | Tmax (h) | Cmax (pmol/mL) | AUCz (pmol * h/mL) | $t_{1/2}$ (h) |
|---|---|---|---|---|---|---|
| A) ST1469 | ST1469 | Mean | 1.8 | 280 | 1480 | 2.9 |
| | | SD | 1.3 | 123 | 780 | 0.8 |
| | | CV % | 68.6 | 43.8 | 52.7 | 28.5 |
| | ST1469 ST2087 | Mean | 3.2 | 447 | 4110 | 4.9 |
| | | SD | 2.8 | 103 | 3106 | 1.3 |
| | | CV % | 87 | 23.1 | 75.6 | 25.9 |

| Treatment | Analyte | | Tmax (h) | Cmax (pmol/mL) | AUCz (pmol * h/mL) | $T_{1/2}$ (h) |
|---|---|---|---|---|---|---|
| B) ST2087 | ST2087 | Mean | 2.0 | 4089 | 32227 | 4.4 |
| | | SD | 1.0 | 2025 | 21078 | 1.2 |
| | | CV % | 50.0 | 49.5 | 65.4 | 26.8 |

Evaluation of the Antipsychotic Potency of ST1469 and ST1899 and their Respective Desmethyl Derivatives ST2087 and ST2472. Effect of Treatment in the Active Avoidance Test.

The administration of incremental doses of an antipsychotic drug in the rat causes the inhibition of the avoidance response and an increase in the number of escape responses without any increase in non-responses (failures). This modification of the avoidance behaviour of the animals is characteristic of the effect of the administration of a compound with antipsychotic activity, which selectively blocks the conditioned response within given dosage ranges. This behavioural assessment makes it possible to detect and determine the antipsychotic capacity of a product.

Experimental Procedure

Male Fischer 344 rats weighing 180 g (Charles River) were used. The products ST1469 and ST2087 were administered to the animals orally, 60 minutes prior to the test. The product ST1469 was administered at doses of 0.75 mg/5 ml/kg (1.84 μmol/kg), 1.5 mg/5 ml/kg (3.69 μmol/kg), 3 mg/5 ml/kg (7.37 μmol/kg), and 6.0 mg/5 ml/kg (14.7 μmol/kg).

For the product ST2087 the following doses were used: 2 mg/5 ml/kg (6.25 μmol/kg), 3 mg/5 ml/kg (9.38 μmol/kg), 4 mg/5 ml/kg (12.50 μmol/kg), 6 mg/5 ml/kg (18.76 mmol/kg) and 8 mg/5 ml/kg (25.01 μmol/kg).

For the evaluation of the antipsychotic potency of the product ST 1899 and its derivative ST2472, each compound was administered respectively at doses of: 0.75 mg/5 ml/kg (μmol/kg), 1.5 mg/5 ml/kg (μmol/kg), 3 mg/5 ml/kg (μmol/kg); and 0.25 mg/5 ml/kg (0.88 μmol/kg), 0.5 mg/5 ml/kg (1.76 μmol/kg), 1.05 mg/kg (3.71 μmol/kg) and 2 mg/kg (7.06 μmol/kg).

To perform the avoidance behaviour assessment test, a piece of equipment (Ugo Basile) was used consisting of a plastic cage divided into two compartments by a partition wall with an opening in it allowing communication between the two sectors. Each of the two sectors can be illuminated by a 10-Watt lamp placed above a plexiglass cover covering the cage. A programming device permits the regulation of the duration and frequency of the un-conditioned and discriminatory stimuli, and a computerised system acquires the experimental data. During the study the discriminatory stimulus (light was delivered 3 seconds prior to the unconditioned stimulus (0.3 mA electric shock for 4 seconds). One test per minute was performed in each session making a total of 20 tests per day. One session per day administered.

The procedure consists in a 1 minute period of familiarisation of the rats in the test cage, followed by the series of tests the start of which is signalled by the light stimulus; the discriminatory stimulus is followed, a few seconds later, by the administration of an electric shock. The rats can avoid the shock by escaping into the adjoining compartment. The responses produced after switching on the light and before the electric shock interrupt the discriminatory stimulus and are considered "avoidances"; the responses produced during the shock period terminate both the discriminatory stimulus and the unconditioned stimulus and are considered "escapes"; non-avoidances are considered "failures".

Prior to the treatment with the study compounds, the animals were selected in relation to their ability to acquire the task. Admitted to the test assessing the effect of treatment were those rats that produced at least 75% of avoidances in the basal tests.

The results were expressed as means and standard errors. On the basis of the number of conditioned responses (avoidances), the dose of product capable of reducing the value of this variable by 50% ($ED_{50}$) compared to basal values was calculated by means of non-linear regression using the GraphPad Prism data analysis program.

Results

Effect of ST1469 and ST2087

The product ST1469 inhibits the ability of the animals to produce an avoidance response in a dose-dependent manner.

The study product ST2087, administered orally, is capable of reducing the production of avoidance responses of the animals at the doses of 2 mg/kg (6.25 μmol/kg), 3 mg/kg (9.38 μmol/kg), 4 mg/kg (12.50 μmol/kg), 6 mg/kg (18.76 μmol/kg) and 8 mg/kg (25.01 μmol/kg). The value of the dose capable of reducing the production of avoidance responses by 50% ($ED_{50}$) is 3.27 mg/kg corresponding to 10.22 μmol/kg.

The data obtained in this study show that the efficacy of the compound ST2087 is similar to that of the compound of origin ST1469 ($ED_{50}$: 3.71 mg/kg corresponding to 9.11 μmol/kg) (Table 2).

Effect of ST1899 and ST2472

Treatment with ST2472 causes a progressive reduction of the avoidance responses and an increase in escapes at the doses of 0.5 mg/kg (1.76 μmol/kg), 1.05 mg/kg (3.71 μmol/kg) and 2 mg/kg (7.06 μmol/kg); at the doses of 0.5 mg/kg and 1.05 mg/kg the failure rate proves particularly limited. Treatment with 0.25 mg/kg (0.88 μmol/kg) does not significantly modify the behaviour of the animals.

The dose capable of reducing the production of the conditioned response by 50% ($ED_{50}$) compared to basal values is 1.43 mg/kg (5.05 μmol/kg) (Table 2).

The test allowed an adequate assessment of the anti-psychotic capacities of this molecule, which prove comparable to those measured for the product of origin ST1899 (Table 2).

TABLE 2

Active Avoidance Test. Oral treatment with the substances indicated. The table gives the $ED_{50}$ values, calculated on the basis of the avoidance rate variable.

| Compound | $ED_{50}$ |
|---|---|
| ST2087 | 3.27 mg/kg |
|  | 10.22 μmol/kg |
| ST1469 | 3.71 mg/kg |
|  | 9.11 μmol/kg |
| ST2472 | 1.43 mg/kg |
|  | 5.05 μmol/kg |
| ST1899 | 1.09 mg/kg |
|  | 3.66 μmol/kg |

Example 6

In Vitro Metabolic Stability of ST1899 and its N-demethylated Metabolite ST2472

In this study the metabolic profiles of ST1899 and its metabolite ST2472 were determined in rat, mouse and monkey microsomes.

Materials and Methods

ST1899 and ST2472 were separately incubated with the hepatic microsomes. Separate experiments were carried out for each animal species investigated. For each experiment, in addition to the test item, 7-ethoxycoumarin (Sigma-Aldrich) was also incubated as a probe for evaluating the metabolic activity of the microsomes: 7-hydroxycoumarin was identified on the basis of the retention times in comparison with those of synthesized standard and used as marker of oxidative metabolism Both the test item and the 7-ethoxycoumarin were incubated at 37° C. up to 120 minutes.

Microsomes information are summarized in the following Table 3:

TABLE 3

| Species | Strain | Sex | Supplire |
|---|---|---|---|
| Mouse | CD1 | Male | Prassis |
| Rat | Sprague Dawley | Male | Prassis |
| Monkey | Cynomolgus | Male | In Vitro Technologies |

The test items, microsomes and reagents nominal concentrations used in the samples are reported in the following Table 4:

TABLE 4

| Substance | Concentration |
|---|---|
| ST1899 | 10 μg/ml |
| ST2472 | 10 μg/ml |
| 7-ethoxycoumarin | 10 μg/ml |
| Microsomes | 0.5 mg/ml |
| $MgCl_2$ | 4 mM |
| β-D-glucose-6-phosphate | 10 mM |
| βNADP | 1 mM |
| Glucose-6-phosphate dehydrogenase | 1.5 units/ml |
| Saccharic acid 1,4 lactone | 5 mM |

$MgCl_2$, β-D-glucose-6-phosphate, βNADP and Glucose-6-phosphate dehydrogenase were used for preparing the NADPH regenerating solution (NRS). 250 μl of 0.1 M pH 7.4 $KH_2PO_4$ buffer, 100 μl of NRS and 50 μl of test item (or 7-ethoxycoumarin) standard solution were added to 2 ml Eppendorf test tubes. In the samples, incubated either without microsomes or test items, an equal volume of 0.1 M pH 7.4 KH2PO4 buffer was added.

The reaction was started by adding 100 μl of the microsomal suspension to the samples and stopped at selected times by adding 500 μl of methanol. Samples were shaken and centrifuged at 8000 RPM for 10 minutes at 4° C. Supernatants were used for the HPLC analysis. 7-ethoxycoumarin, ST1899 and ST2472 were analyzed according to the HPLC methods described below.

HPLC Conditions

HPLCJasco PU-2080 plus, intelligent HPLC pump equipped with Jasco LG-2080-02 ternary gradient unit and Jasco DG-2080-53 3 line degasser (or equivalents). Jasco AS-950 intelligent autosampler (or equivalent).

Flush: $H_2O/CH_3OH$ 50/50; 3 flushes.

Detector Jasco UV-1575 Intelligent UV/VIS detector (or equivalent);

λ 320 nm; Mode NORMAL; response STD.

Column Luna (Phenomenex) C18, 150×4.60 mm, 3 μm; with C18 SecurityGuard

Mobile phase A: 0.5% (v/v) acetic acid

Mobile phase B: Acetonitrile

Injection volume 10 μl

Flow rate 0.8 ml/min

Run time: 25 minutes

Gradient elution program:

| Time (min.) | % A | % B |
|---|---|---|
| 0 | 93 | 7 |
| 5 | 80 | 20 |
| 13 | 40 | 60 |
| 18 | 40 | 60 |
| 19 | 93 | 7 |
| 24 | 93 | 7 |

7-Ethoxycoumarin retention time: about 18 minutes.

7-Hydroxycoumarin retention time: about 12 minutes

Results

Incubation with ST1899

Figure 2:
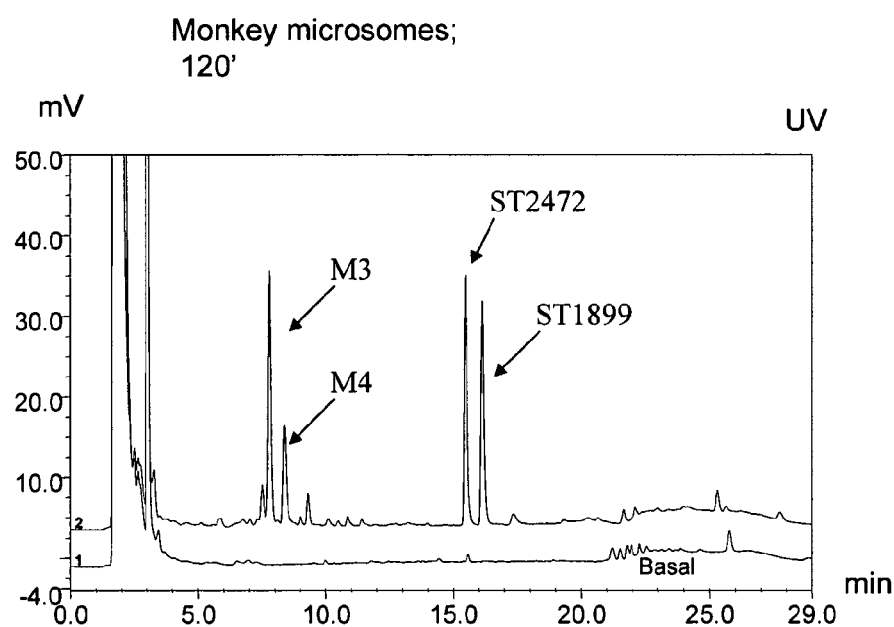
FIG. 2: Metabolic profile obtained for ST1899 monkey microsomes at 120 minutes in comparison to the basal. Results of the HPLC analysis of the supernatants after incubation with the hepatic microsomes

In rat microsomes ST1899 is extensively metabolized to ST2472 (FIG. 1) metabolites M1 and M2 were also present as major metabolites. ST1899 in a mouse microsomes is metabolized mainly to M1 (FIG. 1); ST2472 is also generated but to a limited extent. Two other metabolites, which may be M3 and M4, were found: their intensity changed during the incubation (FIG. 1) and M4 predominated at 120 minutes. In monkey microsomes ST1899 was metabolized to ST2472 and to the metabolites M3 and M4 (FIG. 2). Only small amounts of the metabolite M1 were generated.

Incubation with ST2472

ST2472 in rat microsomes was almost exclusively metabolized to M2 (FIG. 3); therefore it may be hypothesized that metabolites M1 and M2 arise from ST1899 and ST2472 metabolism, respectively.

Figure 3:
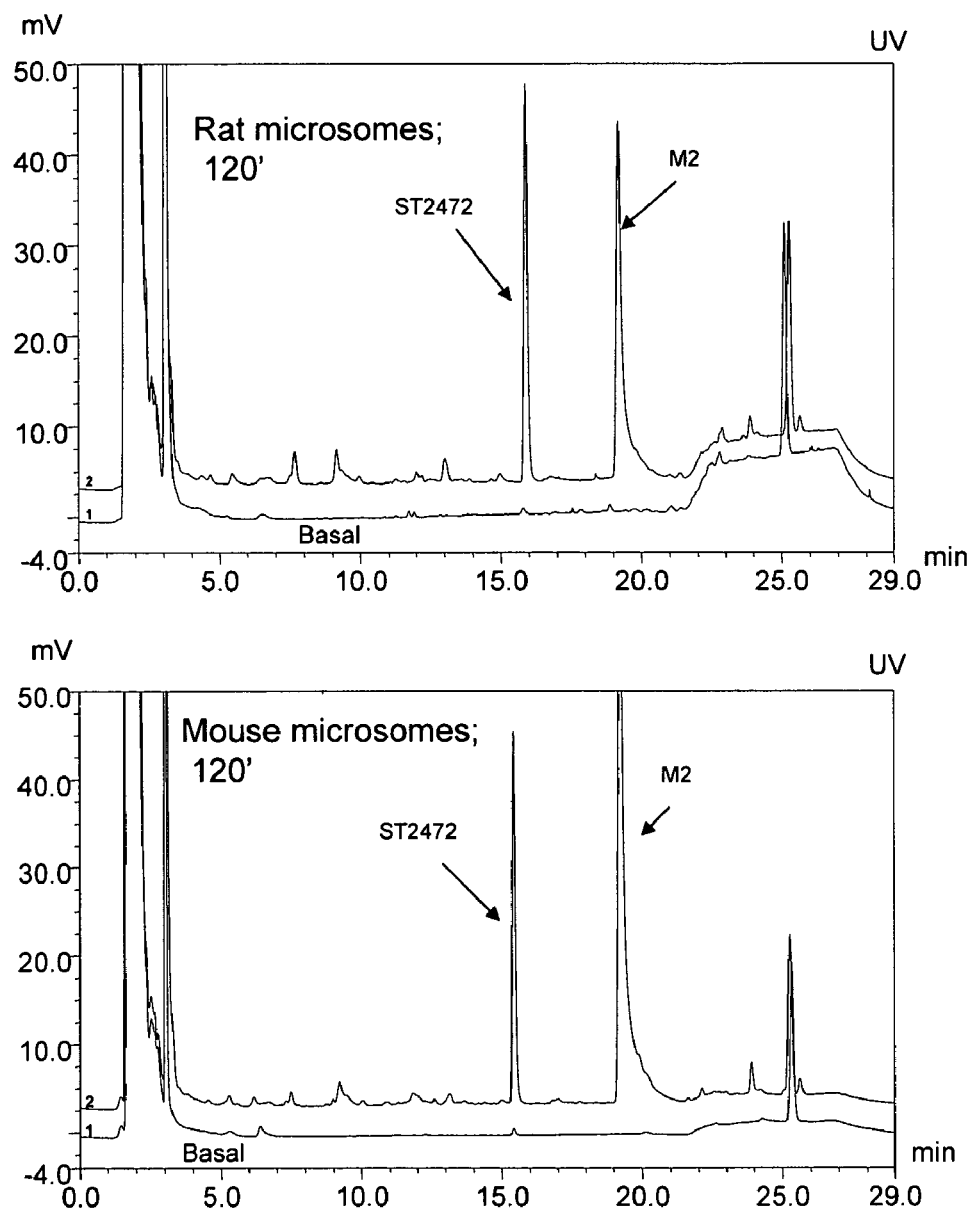
FIG. 3: Metabolic profile obtained for ST2472 in rat and mouse microsomes at 120 minutes in comparison to the basal. Results of the HPLC analysis of the supernatants after incubation with the hepatic microsomes

In mouse microsomes ST2472 was metabolized almost exclusively to M2 (FIG. 3). The metabolite M2 was also present in samples incubated with ST1899, where it may arise from sequential metabolism of ST1899 to ST2472 and then to M2.

Figure 4:
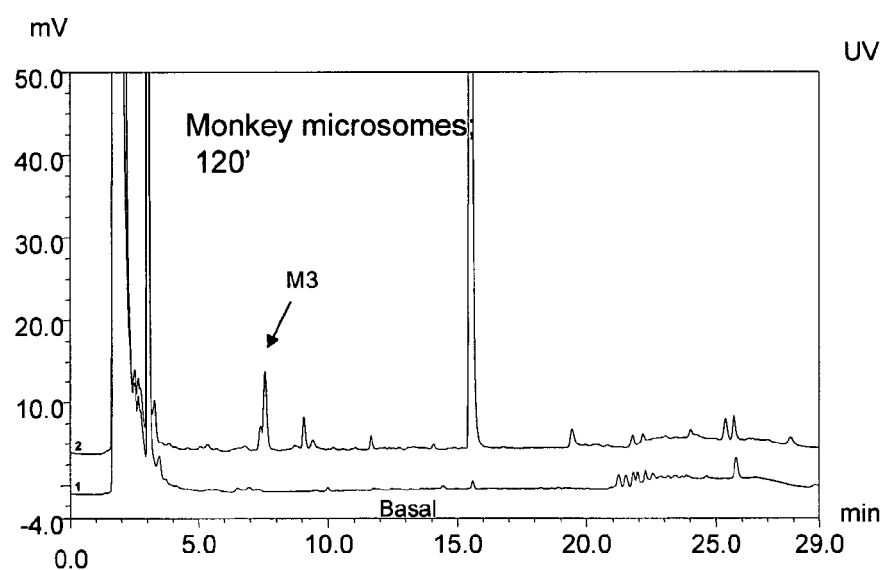
FIG. 4: Metabolic profile obtained for ST2472 in monkey microsomes at 120 minutes in comparison to the basal. Results of the HPLC analysis of the supernatants after incubation with the hepatic microsomes.

ST2472 was metabolically more stable than ST1899: the main metabolite obtained was M3 (FIG. 4). Only small amounts of the metabolite M2 were formed.

The N-demethylation of ST1899 to provide ST2472 is a metabolic biotransformation quantitatively prominent in rats. This metabolism is thought to be also responsible for the low bioavailability of ST1899 orally administered in rats because of an extensive hepatic first pass effect. This metabolic reaction was found to be extensive also in the other species investigated in this study. Incubation of ST1899 in rat, mouse and monkey microsomes led to formation of two or three metabolites other than ST2742, producing a rapid decrease of ST1899 concentration in the medium.

On the other hand, the incubation of ST2472 in rat, mouse and monkey microsomes was characterised by a lower extent of metabolism, which produced a single metabolite although different among rodent and non rodent species.

In conclusion, ST2742 resulted metabolically more stable than ST1899 in all the species tested and this is indicative of a higher bioavailavility and a longer systemic half-life of the parent drug after oral administration.

The invention claimed is:

1. Formula (I) compounds:

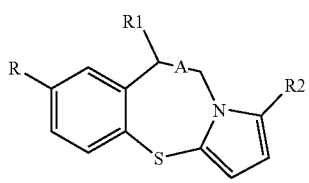

wherein

A is CH—$CH_2$ or C=CH;

R is hydrogen, halogen, alkoxy $C_1$-$C_4$, alkylthio $C_1$-$C_4$, alkyl $C_1$-$C_4$ or cycloalkyl $C_5$-$C_6$;

$R_1$ is 1-piperazinyl, 1-homopiperazinyl or 1-piperidinyl;

$R_2$ is hydrogen, alkoxy $C_1$-$C_4$, alkylthio $C_1$-$C_4$, alkyl $C_1$-$C_4$, CHO, CH=NOH or $CH_2$HO;

provided that when R is Cl, A is not C=CH their single optical isomers, mixtures thereof, and their pharmaceutically acceptable salts.

2. Compound according to claim 1, selected from the group consisting of:

(+)-9-(piperazin-1-yl)-9,10-dihydropyrrolo[2,1-b][1,3] benzothiazepine;

(−)-9-(piperazin-1-yl)-9,10-dihydropyrrolo[2,1-b][1,3] benzothiazepine;

(±)-7-chloro-9-(piperazin-1-yl)-9,10-dihydropyrrolo[2,1-b][1,3]-benzothiazepine;

(S)-7-chloro-9-(piperazin-1-yl)-9,10-dihydropyrrolo[2,1-b][1,3]-benzothiazepine;

(R)-7-chloro-9-(piperazin-1-yl)-9,10-dihydropyrrolo[2,1-b][1,3]-benzothiazepine;

(+)-7-fluoro-9-(piperazin-1-yl)-9,10-dihydropyrrolo[2,1-b][1,3]-benzothiazepine;

9-(piperazin-1-yl)-pyrrolo[2,1-b][1,3]benzothiazepine;

7-fluoro-9-(piperazin-1-yl)-pyrrolo[2,1-b][1,3]benzothiazepine; and 1-methyl-9-(piperazin-1-yl)-pyrrolo[2,1-b][1,3]benzothiazepine.

3. Procedure for the preparation of compounds according to claim 1, comprising the following stages:

(a) treatment of the corresponding 4-alkyl-(homo)piperazin-1-yl-pyrrolo[2,1-b]benzothiazepine or 4-alkyl-piperidin-1-yl-pyrrolo-[2,1-b]benzothiazepine or 4-alkyl-(homo)piperazin-1-yl-dihydropyrrolo-[2,1-b]benzothiazepine or 4-alkyl-piperidin-1-yl-dihydropyrrolo[2,1-b]-benzothiazepine, with the desired alkyl-chloroformiate to give the corresponding carbamate of the nitrogen atom at position 4 of the (homo)piperazine or piperidine ring;

(b) subsequent hydrolysis of the carbamate thus obtained, releasing said nitrogen atom (c) possible salification of the compound obtained in stage b).

4. Procedure for the preparation of compounds according to claim 1 comprising the following stages:

a) treatment of the corresponding 9-keto-pyrrolo[2,1-b] thiazepine or 9-keto-pyrrolo[2,1-b]benzothiazepine or 9-keto-dihydropyrrolo-[2,1-b]benzothiazepine or 9-keto-dihydropyrrolo[2,1-b]benzothiazepine with p-toluenesulphonic acid and piperazine hexahydrate, so as to yield the corresponding enamine;

b) subsequent reduction of the corresponding enamine with hydrides in acetic acid, to yield the corresponding saturated product;

c) possible salification obtained in stage b).

5. Pharmaceutical compositions containing at least one compound according to claim 1 in a mixture with pharmaceutically acceptable vehicles and/or excipients.

6. A method for treating acute and chronic psychotic disorders selected from the group consisting of schizophrenia, paranoid states, manic-depressive states, disorders of the affective sphere, social regression, personality regression, hallucination, appetite disorders and related disorders, said method comprising administering an effective amount of a compound according to claim 1 to a mammal in need thereof.

7. Method according to claim 6 wherein between carbon atoms 9 and 10 there is a single bond and R is hydrogen, fluorine, or bromine.

8. Method according to claim 6 wherein between carbon atoms 9 and 10 there is an unsaturated bond.

9. Method of claim 6, wherein said effective amount comprises from about 1 mg/day to about 200 mg/day.

10. Method for preparing a compound of formula (II)

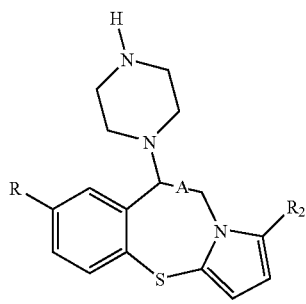

formula (II)

wherein
  A is CH—CH$_2$ or C═CH;
  R is Cl or H;
  R$_2$ is H;
  provided that when R is Cl, A is not C═CH, said method comprising:
a) reacting a compound of formula (III) with an alkylchloroformiate

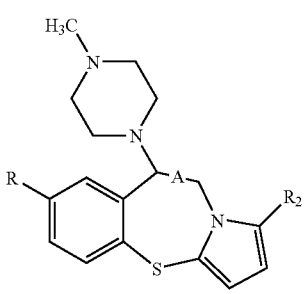

formula (III)

to form a compound of formula (IV)

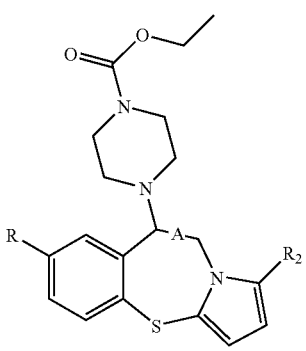

formula (IV)

and
b) hydrolizing said compound of formula (IV) to obtain a compound of formula (II).

11. Method for preparing a compound of formula (V)

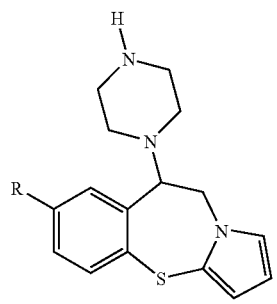

formula (V)

wherein R is Cl, said method comprising:
a) reacting a compound of formula (VI) with p-toluenesulphonic acid and piperazine

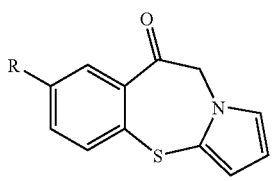

formula (VI)

wherein R is H or Cl
to form a compound of formula (VII)

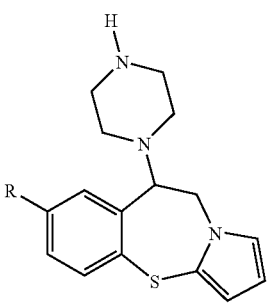

formula (VII)

wherein R is H or Cl; and
c) reducing said compound of formula (VII) with hydrides in acetic acid to obtain a compound of formula (V).

* * * * *